United States Patent [19]

Wagner

[11] 4,187,355
[45] Feb. 5, 1980

[54] PRODUCTION OF POLYALKYLENE GLYCOL ETHERS FROM FORMOSE AND USE THEREOF IN THE PREPARATION OF POLYURETHANE RESINS

[75] Inventor: Kuno Wagner, Leverkusen, Fed. Rep. of Germany

[73] Assignee: Bayer Aktiengesellschaft, Leverkusen, Fed. Rep. of Germany

[21] Appl. No.: 934,578

[22] Filed: Aug. 17, 1978

Related U.S. Application Data

[63] Continuation-in-part of Ser. No. 829,173, Aug. 30, 1977.

[30] Foreign Application Priority Data

Aug. 23, 1977 [DE] Fed. Rep. of Germany ....... 2737951

[51] Int. Cl.$^2$ .............................................. C08G 18/14
[52] U.S. Cl. ...................................... 521/158; 528/77; 528/249; 528/250; 536/120
[58] Field of Search ................ 536/120; 528/249, 250, 528/77; 521/158

[56] References Cited

U.S. PATENT DOCUMENTS 3,202,620  8/1965  Merten et al. ..................... 521/158
3,846,347  11/1974  Satterly ............................. 521/159

OTHER PUBLICATIONS

Partridge et al., Carbohydrate Research 24, 1972, pp. 29–44.

Primary Examiner—Maurice J. Welsh
Attorney, Agent, or Firm—Gene Harsh; Joseph C. Gil

[57] ABSTRACT

This invention relates to a process for the production of novel polyalkylene glycol ethers based on a mixture of polyhydric alcohols, hydroxyaldehydes and hydroxy ketones produced by the auto-condensation of formaldehyde hydrate (formose). The improvement realized is in the use of an acid catalysis rather than the normal base catalysis. The new polyether polyols are valuable starting materials for the production of polyurethane foams.

11 Claims, No Drawings

PRODUCTION OF POLYALKYLENE GLYCOL ETHERS FROM FORMOSE AND USE THEREOF IN THE PREPARATION OF POLYURETHANE RESINS

BACKGROUND OF THE INVENTION

This application is a continuation-in-part application of Ser. No. 829,173, filed Aug. 30, 1977.

Processes for the production of polyalkylene glycol ethers are known. Conventional processes for the production of polyethers are based on the polymerization of epoxides on their own or on the addition of these epoxides with starter components containing reactive hydrogen atoms. Preferred starting components in conventional processes include saccharose (German Auslegeschriften No. 1,064,938 and No. 1,176,358; German Offenlegungsschrift No. 1,443,022), sorbitol (British Pat. No. 876,496, Belgian Pat. No. 582,076 and Modern Plastics, May 1959, pages 151–154) and various difunctional and trifunctional polyhydric alcohols, such as ethylene glycol, propylene glycol, trimethylol propane or glycerol.

Polyether polyols having a hydroxyl functionality of 6 or 8 are obtained by reacting saccharose or sorbitol (or other hexahydric sugar alcohols). Providing they have relatively low molecular weight, these highly functional polyethers are particularly suitable for the production of rigid and semi-rigid polyurethane foams which have good dimensional stability.

For the reaction of saccharose and sorbitol with alkylene oxides on a commercial scale, it is essential that the reaction mixture may be satisfactorily stirred. The intense heating effect which occurs during the reaction of alkylene oxides with hydroxyl compounds may only be adequately dissipated if the reaction mixture is vigorously stirred.

However, mixtures of alkylene oxides with saccharose or sorbitol cannot be satisfactorily stirred under the conditions applied in the commercial production of polyethers, i.e. temperatures of from 95° to 115° C. and pressures of from 0.5 to 3.5 atmospheres gauge. The problem of stirrability particularly occurs in the case of saccharose at the beginning of the alkylene oxide addition when large quantities of unreacted, solid starter material are still present. Inadequately stirrable mixtures of saccharose and alkali metal hydroxide, which is generally used as catalyst in the production of polyethers, may give rise to caramelization and carbonization reactions on the walls of the reaction vessel which inevitably become hot when the reaction mixture is heated. Mixtures of sorbitol and alkylene oxides are also very difficult to stir in the presence of large quantities of unreacted sorbitol, because sorbitol is still present as a solid or just begins to melt at the reaction temperatures (m.p. 97.7° C.). The melts obtained are relatively highly viscous.

Overheating in sorbitol melts, which may easily occur in inadequately stirred reaction mixtures, may give rise in the presence of alkali metal hydroxides to the formation of so-called "sorbitol anhydrides", known as "sorbitans", which in turn results in a loss of functionality in the resulting polyethers. This results in deterioration of the properties of the rigid polyurethane foams produced therefrom.

In order to obviate these disadvantages, it has been proposed to use mixtures of saccharose or sorbitol with low viscosity difunctional or trifunctional polyhydric alcohols as starting components (German Auslegeschrift No. 1,285,741; German Offenlegesschriften Nos. 2,443,372; 2,241,242; 2,521,739 and 2,549,449) or aqueous solutions of the more highly functional starters.

However, the reaction of saccharose or sorbitol with alkylene oxide in aqueous solution or in admixture with glycols is accompanied by undesirable secondary reactions, for example partial hydrolysis of the alkylene oxide by the water used as reaction medium. The hydrolyzed alkylene oxide, the polyalkylene glycols formed therefrom by reaction with more alkylene oxide, and the other secondary products formed (whose presence is reflected in pronounced darkening in the color of the reaction mixture), adversely affect the properties of the rigid and semi-rigid polyurethane foams produced from these saccharose or sorbitol hydroxyalkyl ethers.

One disadvantage of the rigid polyurethane foams produced from saccharose polyethers produced in this way is their often small proportion of closed cells and their resulting poor heat insulating capacity.

In addition, the high proportion of bifunctional and trifunctional secondary products in polyethers of this type means that the rigid polyurethane foams produced from these polyether mixtures do not show significantly reduced dimensional stability.

Polyether polyols which have been obtained by reacting saccharose and/or saccharose/glycol mixtures and which have average molecular weights of from 500 to 1500 are relatively high-viscosity liquids. On account of their high viscosity, the fluidity of the final reaction mixture is reduced during the foaming process. This results in the inadequate filling of molds in the case of molded foams. In addition, there is an unequal distribution in density in the polyurethane foam, resulting in a reduction in compression strength.

Polyethers which are suitable for the production of flexible polyurethane foams are generally produced by known methods by reacting trifunctional polyols, such as glycerol or trimethylol propane, with propylene oxide or ethylene oxide or with a mixture of propylene oxide and ethylene oxide. In many cases, the starter component is also initially reacted with propylene oxide and then with ethylene oxide, resulting in the formation of polyethers predominantly containing primary terminal hydroxyl groups.

However, polyurethane foams produced from such polyether polyols are frequently unable to satisfy the demands with regard to compression hardness. Accordingly, in order to obtain flexible polyurethane foams showing increased compression hardness, it has been proposed to mix bifunctional and trifunctional starters with sorbitol or saccharose and to react these mixtures with a large excess of ethylene oxide to form polyether polyols having an average molecular weight of from 1000 to 10,000 (German Offenlegungsschriften Nos. 2,521,739 and 2,549,449). The reaction of sorbitol alone with alkylene oxides to form relatively high molecular weight polyether polyols having a hydroxyl number of from 20 to 60 is also known.

However, in the production of such polyether polyols by conventional processes, difficulties also arise because the mixtures of the starting components either have a paste-like consistency or are liquids of relatively high viscosity at room temperature or moderately elevated temperature. For this reason, starting components of this type cannot readily be pumped through pipes. This necessitates the use of elaborate apparatus when the polyether polyols are produced on a commercial scale.

It is also not readily possible to satisfactorily stir these mixtures vigorously (as in the case of the rigid foam polyethers as well). For this reason, the reaction velocity of the alkylene oxides is reduced, giving rise to poor volume-time yields in the production of the polyether polyols. In addition, secondary products, which are formed by decomposition of the inadequately stirred reaction mixtures on the hot walls of the reaction vessel, lead to polyether polyols with lower hydroxyl functionality then desired. In many cases, yellow to brown-colored polyethers are obtained.

Accordingly, there is a need for a process for producing polyalkylene glycol ethers by which it is readily possible to produce polyether polyols without the unfavorable properties referred to above, produce polyols with the envisioned functionality, and at the same time, largely avoid the disadvantages of conventional processes.

According to an earlier proposal (German Offenlegungsschrift No. 26 39 083), polyether polyols having an average molecular weight of from 200 to 10,000 and an average hydroxyl functionality of from 2.0 to 7.0 are produced by reacting one or more alkylene oxides, optionally successively, with a mixture of polyhydric alcohols which has been produced by the auto-condensation of formaldehyde hydrate. The auto-condensation is followed by reduction of the condensation products and the optional mixing with additional dihydric and/or trihydric alcohols and/or monoamines or polyamines (the mixture of polyhydric alcohols, hydroxy aldehydes and hydroxy ketones produced by the auto-condensation of formaldehyde hydrate will be referred to hereinafter as "formose" and the polyol mixture produced therefrom by hydrogenation as "formitol").

DESCRIPTION OF THE INVENTION

Further development of the process according to the above-mentioned earlier Application has now surprisingly shown that polyether polyols having excellent properties may be directly obtained in a simple, economic and reproducible manner by alkoxylating formose in the presence of strongly acid catalysts.

Accordingly, the present invention relates to a process for the production of polyether polyols having an average molecular weight of from 200 to 10,000 and an average hydroxyl functionality of from 2.0 to 7.0, preferably from 2.5 to 6.0 and, with particular preference, from 2.8 to 5.5. These polyols are made by reacting one or more cyclic ethers, optionally successively, with a starter comprising (A) formose (optionally α-aldolized) or (2) liquid mixtures of formose with high molecular weight and/or low molecular weight polyhydroxyl compounds, monosaccharides or disaccharides, and/or natural or artificial invert sugars and formose which is optionally α-aldolized in the presence of an acid catalyst.

It may be regarded as surprising that high-quality products with little or no color are reproducibly obtained without any troublesome secondary reactions (for example dehydration of sugars accompanied by darkening) by the process according to the present invention. If, for example, an attempt is made to alkoxylate formose by base-catalyzed ring-opening polyaddition reactions with oxiranes, numerous, largely unknown secondary reactions occur accompanied by pronounced blackening of the reaction mixture. It is not possible in this way to produce standardized polyethers based on formose. On the other hand, it is also not possible to alkoxylate conventional starters for polyethers based on sugar (for example glucose or cane sugar) by means of acid catalysts. In the process according to the present invention, addition of the cyclic ethers to the hydroxyl groups of the formose is surprisingly accompanied to a large extent by acetalization or ketalization reactions on the carboxyl functional group of the formose. The advantage of this is that, when the polyether polyols obtained are used for the production of polyurethane foams, there are no caramelization reactions. Such caramelization reactions produce a characteristic, unpleasant odor, and are accompanied by discoloration of the foam core. These reactions occur in the case of conventional sugar polyethers.

Formoses of any type may be used in the process according to the present invention. The production of mixtures of polyhydric alcohols, hydroxy aldehydes and hydroxy ketones by the auto-condensation of formaldehyde hydrate is described in numerous literature references. In this connection, reference may be made, for example, to Butlerow and Loew, Annalen 120, 295 (1861), and J. pr. Chem. 33, 321 (1886); Pfeil, Chemische Berichte 84, 229 (1951); Pfeil and Schroth, Chemische Berichte 85, 303 (1952); R. D. Partridge and A. H. Weiss, Carbohydrate Research 24, 29–44 (1972); the formoses of glycerol aldehyde and dioxyacetone according to Emil Fischer; German Pat. Nos. 882,385; 330,951 and 884,794, U.S. Pat. Nos. 2,224,910; 2,269,935 and 2,272,378 and British Pat. No. 513,708. However, these conventional processes are attended by a number of disadvantages (toxic catalysts, poor volume-time yields, discolored secondary products). According to the present invention, therefore, it is preferred to use as starters formoses which have been produced by certain new processes which are the subject of previously filed applications.

One of these new processes comprises condensing formaldehyde hydrate in the presence of soluble or insoluble lead (II) salts, optionally fixed to high molecular weight supports, as catalysts and in the presence as co-catalyst of a mixture of hydroxy aldehydes and hydroxy ketones such as is formed in the condensation of formaldehyde hydrate and which is characterized by the following molar ratios: Compounds containing 3 carbon atoms/compounds containing 4 carbon atoms:

0.5:1–2.0:1

Compounds containing 4 carbon atoms/compounds containing 5 carbon atoms:

0.2:1–2.0:1

Compounds containing 5 carbon atoms/compounds containing 6 carbon atoms:

0.5:1–5.0:1

The proportion of components containing from 3 to 6 carbon atoms amounts to at least 75%, by weight, preferably to more than 85%, by weight, based on the total co-catalyst.

The reaction temperature is generally from 70° to 110° C., preferably from 80° to 100° C. The pH value of the reaction solution is adjusted by the controlled addition of an inorganic or organic base up to a conversion of from 10 to 60%, preferably from 30 to 50%, to a value of from 6.0 to 8.0, preferably 6.5 to 7.0, and then to a value of from 4.0 to 6.0, preferably from 5.0 to 6.0. It was surprisingly found that the product distribution of the corresponding polyol, hydroxy aldehyde and hydroxy ketone mixtures may be reproducibly varied by this particular pH profile and by subsequent cooling at different residual formaldehyde contents (from 0 to 10%, by weight, preferably from 0.5 to 6%, by weight).

After the auto-condensation of the formaldehyde hydrate has been interrupted by cooling and/or by deactivating the lead-containing catalyst with acids, the catalyst is removed in known manner and the water present in the products is evaporated. For further particulars, reference may be made to German Offenlegungsschrift No. 2,639,084.

Another possibility for obtaining highly concentrated, colorless formoses in high volume-time yields is to condense aqueous formalin solutions and/or paraformaldehyde dispersions in the presence of a soluble or insoluble metal catalyst and a co-catalyst produced by partial oxidation of a dihydric or polyhydric alcohol containing at least two adjacent hydroxyl groups and having a molecular weight of from 62 to 242 or a mixture of such alcohols. The pH value of the reaction solution is maintained at from 6.0 to 9.0 by the controlled addition of a base up to a conversion of from 5 to 40%. The reaction mixture is subsequently adjusted to from 4.5 to 8.0 to terminate the condensation reaction in such a way the pH value is then from 1.0 to 2.0 units lower than in the first phase of the reaction. The reaction is then interrupted by deactivating the catalyst at a residual formaldehyde content of from 0 to 10% by weight, and the catalyst is then removed. This process is described in detail in German Offenlegungsschrift No. 2,714,084.

It is also possible to use formoses which have been produced by the condensation of formaldehyde in the presence of a metal catalyst and more than 10%, by weight, based on formaldehyde, of one or more dihydric or polyhydric low molecular weight alcohols and/or relatively high molecular weight polyhydroxyl compounds. Such formosepolyol mixtures are the subject of German Offenlegungsschrift No. 2,714,104.

It is particularly economic to produce formose directly from formaldehyde-containing synthesis gases, i.e. without resorting to the use of aqueous formalin solutions or paraformaldehyde. To this end, the synthesis gases, such as are obtained in the commercial production of formaldehyde, are passed continuously or at intervals at temperatures of from 10° to 150° C. into an absorption liquid which consists of water, monohydric or polyhydric low molecular weight alcohols and/or relatively high molecular weight polyhydroxyl compounds and/or compounds capable of endiol formation as co-catalyst and/or soluble or insoluble metal compounds, optionally fixed to high molecular weight supports, as catalyst and which has a pH value of from 3 to 10. The formaldehyde is directly condensed in situ in the absorption liquid (or even in a following reaction tube or a following cascade of stirrerequipped vessels). Auto-condensation of the formaldehyde is stopped at a residual formaldehyde content in the reaction mixture of from 0 to 10%, by weight, by cooling and/or by deactivating the catalyst with acids and the catalyst is finally removed. Particulars of this process can be found in German Offenlegungsschriften Nos. 2,721,093 and 2,721,186.

According to the present invention, it is, of course, also possible to use formoses which have been converted into the corresponding semiacetals by reaction with excess formaldehyde or which have been α-methylolated by reaction with formaldehyde in the presence of bases. Modified formoses of this type are also described in detail in German Offenlegungsschrift No. 2,721,186.

The properties of the formose (average hydroxyl functionality; degree of branching; and content of reducing groups) may be varied within wide limits, depending upon the manner in which condensation of the formaldehyde is carried out. In general, the average molecular weight, and hence, the hydroxyl functionality of the formoses is increased as the condensation reaction is continued, i.e. the smaller the quantity of residual formaldehyde present when the condensation reaction is terminated. Thus, if the condensation reaction is continued up to a residual formaldehyde content of from 0 to 1.5%, by weight, the formose obtained contains approximately 25%, by weight, of compounds containing 5 carbon atoms, 45%, by weight, of compounds containing 6 carbon atoms and approximately 20%, by weight, of compounds containing 7 or more carbon atoms. By contrast, a total of only about 10% of polyols, hydroxy ketones and hydroxy aldehydes containing 2, 3 and 4 carbon atoms is obtained. This corresponds to an average hydroxyl functionality of approximately 5. Polyethers produced in accordance with the present invention by alkoxylating a starter mixture of this type are eminently suitable for the production of rigid polyurethane foams.

As explained above, however, other component distributions of the starter mixtures are also obtained by terminating auto-condensation of the formaldehyde at somewhat higher residual formaldehyde contents. Thus, termination of the condensation reaction at a formaldehyde content of from 2 to 2.5% gives a mixture of polyhydric alcohols, hydroxy aldehydes and hydroxy ketones having an average hydroxyl functionality of approximately 4. A polyether which is eminently suitable for the production of rigid polyurethane foams is obtained therefrom by propoxylation.

Other component distributions having lower average hydroxyl functionality are obtained by terminating the condensation reaction at residual formaldehyde contents of greater than 2.5. These starter mixtures of low hydroxyl functionality may be reacted to form polyethers which are eminently suitable for the production of flexible polyurethane foams. Their viscosity is lower than that of conventional commercial-grade polyethers based on trimethylol propane and glycerol having the same functionality. This leads to improved properties of polyurethane foams produced therefrom. The lower viscosity provides for a distinct improvement in the fluidity of the final reaction mixture. This leads, for example, to more uniform filling of foaming molds.

According to the present invention, it is preferred to use formoses having an average molecular weight of from 92 to 360, particularly from 100 to 240, and a content of reducing compounds (expressed as glucose) of from 4 to 85%, by weight, and, with particular preference, from 6 to 72%, by weight.

By mixing the formose with difunctional or more highly functional low molecular weight alcohols, the functionality of the starter mixture may optionally be further varied to obtain various particular properties of the resulting polyethers. Suitable low molecular weight polyhydric alcohols of this type (molecular weight up to approximately 300) include ethylene glycol, 1,2-propane diol, 1,3-propane diol, 1,4-butane diol, diethylene glycol, dipropylene glycol, triethylene glycol, tetraethylene glycol, dibutylene glycol, glycerol, trimethylol propane, pentaerythritol, sorbitol, butane triols and hexane triols as well as ethoxylation products of these alcohols. Even hydrogenated formose (formitol) can be used.

Surprisingly, formose is capable of dissolving relatively large quantities of crystallized monosaccharides and disaccharides, such as glucose, maltose or cane sugar; natural invert sugar (for example bees' honey) or artificial invert sugars, for example hydrolysates of cane sugar; hydrolysates of corn starch, potato starch and of pectins (amylose and amylopectins); as well as hydrolysates of any other disaccharides and/or polysaccharides, for example trehalose, galactose, raffinose, cellulose and dextrins. This is of particular commercial interest because such crystallized monosaccharides cannot be alkoxylated in pure form by the process according to the present invention. Monosaccharides and disaccharides of the type in question are preferably used in the form of a 20 to 80%, by weight, solution (preferably 30 to 70%) in formose. Such solutions may be produced very easily by mixing aqueous sugar solutions with formose and concentrating the solutions, for example in a thin-layer evaporator, to water contents of from about 0.5 to 5%, by weight, preferably from 0.7 to 3.5%, by weight.

Any catalysts of the type known for Friedel-Crafts reactions and for cationically initiated polymerization reactions may be used for the process according to the present invention. Such catalysts include strong inorganic or organic acids, such as sulphuric acid, perchloric acid, chlorosulphonic acid, fluorosulphonic acid, aliphatic and aromatic sulphonic acids, such as methane sulphonic acid, butane sulphonic acid and trifluoromethane sulphonic acid, perfluoroalkane carboxylic acids, benzene sulphonic acid and p-toluene sulphonic acid, Lewis acids, such as iron (III) chloride, iron (III) bromide, antimony (V) chloride, aluminum trichloride, titanium tetrachloride and tin tetrachloride and the corresponding fluorides, boron trichloride, boron trifluoride and addition compounds of the boron halides with ethers, carboxylic acids, carboxylic acid anhydrides, carboxylic acid esters, amines, nitriles and mono- or di-carboxylic acid amides, for example the adducts with diethyl ether, tetrahydrofuran, di-n-butyl ether, anisole, ethyl acetate, acetanhydride, acetonitrile, dimethyl formamide, glacial acetic acid or water. Oxonium salts and carboxonium salts of boron halides, such as triethyloxonium fluoroborate and 2-methyl dioxolenium fluoroborate and fluoroborates or aryl diazonium compounds which change into aryl cations at elevated temperature with elimination of nitrogen, such as p-nitrophenyl thiazonium fluoroborate, are also suitable catalysts for the purposes of the present invention. Examples of other catalysts and catalyst systems suitable for cationic polymerization reactions can be found in German Pat. Nos. 741,478 and 766,208 and in French Pat. No. 898,269. According to the present invention, preferred catalysts are boron trifluoride and adducts of boron trifluoride with acids, anhydrides, mixed anhydrides and cyclic anhydrides. It is particularly preferred to use the adducts of boron trifluoride with acetic acid, propionic acid and acetic acid anhydride. In the process according to the present invention, the catalysts are generally used in a quantity of from 0.001 to 5%, by weight, preferably from 0.05 to 2%, by weight, and, with particular preference from 0.2 to 1%, by weight (based on the total reaction mixture).

The ring-opening cationic polyaddition of cyclic ethers is known to be greatly accelerated by compounds containing active hydrogen atoms, particularly hydroxyl compounds and water. Such co-catalysts include the dihydric and polyhydric alcohols having a molecular weight of from 62 to approximately 300 which were mentioned above as a formose mixture component as well as known hydroxyl group-containing linear or branched polyethers, polyesters, polyacetals and polycarbonates having a molecular weight of from about 300 to 4000, of the type described below as starting components which may optionally be used in the production of polyurethane plastics.

Reaction products of polyols with cyclic acid anhydrides which lead to polyethers containing free carboxyl groups, and compounds modified by urethane groups, of the type obtained in the reaction of the above-mentioned hydroxyl compounds with a less than equivalent quantity of polyisocyanate, are also suitable as co-catalysts for the process according to the present invention. All these co-catalytically active compounds containing hydroxyl groups may be used in basically any quantities in the process according to the present invention, although they are preferably used in quantities of from 2 to 100%, by weight (based on formose).

According to the present invention, it is particularly preferred to use water as co-catalyst. If water is used as co-catalyst, the quantity in which it is used should generally not exceed a maximum of 4%, by weight, based on the starter mixture. It is only when the adducts of boron trifluoride with carboxylic acids or carboxylic acid anhydrides, which represent the particularly preferred catalysts according to the present invention, are used that relatively large quantities of water (from 0.5 to around 20%, by weight, preferably from 0.5 to 10%, by weight) may also be used.

The cyclic ethers used in the process according to the present invention particularly include epoxides containing from 2 to 8 carbon atoms, such as ethylene oxide, propylene oxide, 1,2-butylene oxide, 2,3-butylene oxide, styrene oxide, cyclopentene oxide or cyclohexene oxide. Cyclic ethers containing from 3 to 5 carbon atoms in the ring, such as trimethylene oxide, tetramethylene oxide (tetrahydrofuran) or pentamethylene oxide (tetrahydropyran) may also be used. Halogen-substituted alkylene oxides and alkylene oxides containing olefinic double bonds, such as epichlorohydrin, vinyl oxirane, vinyl cyclohexene oxide or methacrylic acid glycidol ester, are also suitable.

The alkoxylation reaction according to the present invention may be carried out either using only one of the above-mentioned alkylene oxides or mixtures of the alkylene oxides. In the process according to the present invention, it is also possible to use various alkylene oxides successively in the same reaction mixture for producing so-called "block copolyethers". According to the present invention, ethylene oxide and/or propylene oxide are preferably used.

The reaction temperatures may be varied within wide limits in the process according to the present invention. In general, the reaction is carried out at temperatures of from 5° to 120° C., preferably from 20° to 90° C. and, with particular preference, from 30° to 70° C. The reaction with the above-described cyclic ethers may be carried out both under elevated pressure and also under normal pressure or a slightly reduced pressure. It is preferred to apply pressures of from 0.5 to 5 bars, particularly from 1 to 3 bars. The use of an inert gas atmosphere (nitrogen or noble gases) is preferred.

The process according to the present invention may also be carried out in the presence of an inert solvent, such as toluene, xylene or perchlorethylene and the like. However, it is preferably carried out in the absence of solvents.

According to the present invention, the formose (optionally in admixture with sugars and/or polyhydroxyl compounds and/or water) is generally initially introduced into a suitable stirrer-equipped vessel which is repeatedly purged with nitrogen. The catalyst is added with stirring. If it is intended to produce polyethers of high molecular weight in accordance with the present invention, i.e. to add relatively large quantities of cyclic ethers to the starter mixture, it is best initially to introduce only part of the catalyst and then to add the rest of the catalyst at various stages during addition of the cyclic ether. Thereafter, the cyclic ether is stirred, in portions, into the starter mixture. On completion of the polyaddition reaction, the reaction mixture is evacuated in order to remove traces of residual monomers, neutralized and separated from insoluble metal salts by filtration.

The polyethers produced in accordance with the present invention are clear, colorless to yellowish liquids whose viscosity fluctuates according to hydroxyl number and functionality from 400 cP/25° C. (in the case of polyethers having a functionality of 3 and OH-numbers of from 60 to 55) to approximately 30,000 cP/25° C. (for example in the case of polyethers having a functionality of 4.6 and an OH-number of 556). The viscosities of the polyethers obtained are distinctly lower than those of conventional commercial-grade polyethers for comparable functionality and hydroxyl number. By varying the hydroxyl number and component distribution of the starter mixtures and, optionally, the diols and/or triols added, it is possible to produce products whose viscosity is optimally adapted to the particular application envisaged.

The polyether polyols produced in accordance with the present invention, optionally together with other known relatively high molecular weight compounds containing isocyanate-reactive groups and/or chain-extenders, may be reacted with polyisocyanates to form cellular or noncellular polyurethane plastics.

Formose polyethers particularly suitable for the production of rigid polyurethane foams are formose polyethers having OH-numbers of from about 300 to 650. Polyethers having OH-numbers of from about 25 to 60 are preferably used for the production of flexible foams. In addition, the polyether polyols according to the present invention are also valuable intermediate products for the production of emulsifiers and surfactants. They may also be used as thickeners for pigment pastes.

Accordingly, the present invention also relates to a process for the production of optionally cellular polyurethane plastics by reacting:

(a) polyisocyanates; with
(b) relatively high molecular weight compounds containing isocyanate-reactive hydrogen atoms; and, optionally,
(c) chain-extenders; optionally in the presence of
(d) blowing agents, catalysts and other known additives; wherein the polyether polyols produced in accordance with the present invention are used as component (b).

Starting components suitable for use in accordance with the present invention include aliphatic, cycloaliphatic, araliphatic, aromatic and heterocyclic polyisocyanates of the type described for example, by W. Siefken in Justus Liebigs Annalen der Chemie, 562, pages 75 to 136. These include ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3- and 1,4-diisocyanate, also mixtures of these isomers, 1-isocyanato-3,3,5-trimethyl-5-isocyanatomethyl cyclohexane (German Auslegeschrift No. 1,202,785, U.S. Pat. No. 3,401,190), 2,4- and 2,6-hexahydrotolylene diisocyanate, also mixtures of these isomers, hexahydro-1,3- and/or 1,4-phenylene diisocyanate, perhydro-2,4'- and/or 4,4'-diphenylmethane diisocyanate, 1,3- and 1,4-phenylene diisocyanate, 2,4- and 2,6-tolylene diisocyanate, also mixtures of these isomers, diphenyl methane-2,4'- and/or 4,4'-diisocyanate, naphthylene-1,5-diisocyanate, triphenyl methane-4,4',4"-triisocyanate, polyphenyl polymethylene polyisocyanates, of the type which may be obtained by condensing aniline with formaldehyde, followed by phosgenation, and which are described, for example, in British Pat. Nos. 874,430 and 848,671, m- and p-isocyanatophenyl sulphonyl isocyanates according to U.S. Pat. No. 3,454,606, perchlorinated aryl polyisocyanates of the type described, for example, in German Auslegeschrift No. 1,157,601 (U.S. Pat. No. 3,277,138), polyisocyanates containing carbodiimide groups of the type described in German Pat. No. 1,092,007 (U.S. Pat. No. 3,152,162), diisocyanates of the type described in U.S. Pat. No. 3,492,330, polyisocyanates containing allophanate groups of the type described, for example, in British Pat. No. 994,890, Belgian Pat. No. 761,626 and published Dutch patent application No. 7,102,524, polyisocyanates containing isocyanurate groups of the type described, for example, in U.S. Pat. No. 3,001,973, German Pat. Nos. 1,022,789; 1,222,067; and 1,027 394 and in German Offenlegungsschriften Nos. 1,929,034 and 2,004,048, polyisocyanates containing urethane groups of the type described, for example, in Belgian Pat. No. 752,261 or in U.S. Pat. No. 3,394,164, polyisocyanates containing acylated urea groups according to German Pat. No. 1,230,778, polyisocyanates containing biuret groups of the type described, for example, in German Pat. No. 1,101,394 (U.S. Pat. Nos. 3,124,605 and 3,201,372) and in British Pat. No. 889,050, polyisocyanates obtained by telomerization reactions of the type described, for example, in U.S. Pat. No. 3,654,106, polyisocyanates containing ester groups of the type described, for example, in British Pat. Nos. 965,474 and 1,072,956, in U.S. Pat. No. 3,567,763 and in German Pat. No. 1,231,688, also reaction products of the above-mentioned isocyanates with acetals according to German Pat. No. 1,072,385 and polyisocyanates containing polymeric fatty acid radicals according to U.S. Pat. No. 3,455,883.

It is also possible to use the isocyanate group-containing distillation residues obtained in the commercial production of isocyanates, optionally in solution in one or more of the aforementioned polyisocyanates. It is also possible to use mixtures of the aforementioned polyisocyanates.

In general, it is particularly preferred to use the commercially readily available polyisocyanates, for example 2,4- and 2,6-tolylene diisocyanate, also mixtures of these isomers ("TDI"), polyphenyl polymethylene polyisocyanates of the type obtained by condensing aniline with formaldehyde, followed by phosgenation ("crude MDI") and polyisocyanates containing carbodiimide groups, urethane groups, allophanate groups, isocyanurate groups, urea groups or biuret groups ("modified polyisocyanates").

Starting components which may optionally be used in addition to the polyethers produced in accordance with the present invention are compounds containing at least two isocyanate-reactive hydrogen atoms and generally having a molecular weight of from 400 to 10,000. In addition to compounds containing amino groups, thiol groups or carboxyl groups, compounds of this type are preferably polyhydroxyl compounds, more especially compounds containing from two to eight hydroxyl groups, particularly those having molecular weights of from 800 to 10,000, preferably from 1000 to 6000. Such compounds include polyesters, polyethers, polythioethers, polyacetals, polycarbonates and polyester amides containing at least two, generally from 2 to 8, but preferably from 2 to 4 hydroxyl groups, of the type commonly used for the production of homogeneous and cellular polyurethanes.

Examples of suitable polyesters containing hydroxyl groups are reaction products of polyhydric, prefereably dihydric and, optionally, trihydric, alcohols with polybasic, preferably dibasic, carboxylic acids. Instead of the free polycarboxylic acids, the corresponding polycarboxylic acid anhydrides or corresponding polycarboxylic acid esters of lower alcohols or mixtures thereof may also be used for the production of the polyesters. The polycarboxylic acids may be aliphatic, cycloaliphatic, aromatic and/or heterocyclic, and may optionally be substituted, for example by halogen atoms, and/or may be unsaturated.

Examples of these polycarboxylic acids include: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids, such as oleic acid, optionally in admixture with monomeric fatty acids, terephthalic acid dimethyl ester and terephthalic acid-bisglycol ester. Examples of suitable polyhydric alcohols include: ethylene glycol, 1,2- and 1,3-propylene glycol, 1,4- and 2,3-butylene glycol, 1,6-hexanediol, 1,8-octanediol, neopentyl glycol, cyclohexane dimethanol (1,4-bishydroxy methyl cyclohexane), 2-methyl-1,3-propane diol, glycerol, trimethylol propane, 1,2,6-hexane triol, 1,2,4-butane triol, trimethylol ethane, pentaerythritol, quinitol, mannitol, sorbitol, methyl glycoside, also diethylene glycol, triethylene glycol, tetraethylene glycol, polyethylene glycols, dipropylene glycol, polypropylene glycols, dibutylene glycol and polybutylene glycols. The polyesters may contain terminal carboxyl groups. Polyesters of lactones, for example ε-caprolactone, or hydroxy carboxylic acids, for example Ψ-hydroxy caproic acid, may also be used.

Polyethers modified by vinyl polymers of the type formed, for example, by polymerizing styrene and acrylonitrile in the presence of polyethers (U.S. Pat. Nos. 3,383,351; 3,304,273; 3,523,093; and 3,110,695: German Pat. No. 1,152,536), are also suitable, as are polybutadienes containing OH-groups.

Among the polythioethers, particular reference is made to the condensation products of thiodiglycol with itself and/or with other glycols, dicarboxylic acids, formaldehyde, amino carboxylic acids or amino alcohols. Depending upon the co-components, these products are polythio mixed ethers, polythioether esters or polythioether ester amides.

Suitable polyacetals are, for example, those compounds which may be obtained from the reaction of glycols, such as diethylene glycol, triethylene glycol, 4,4'-dioxethoxy diphenyl dimethyl methane and hexane diol, with formaldehyde. Polyacetals suitable for the purposes of the present invention may also be obtained by polymerizing cyclic acetals.

Suitable polycarbonates containing hydroxyl groups are those known compounds obtainable, for example, by reacting diols, such as 1,3-propane diol, 1,4-butane biol and/or 1,6-hexane diol, diethylene glycol, triethylene glycol and tetraethylene glycol, with diaryl carbonates, for example diphenyl carbonate, or with phosgene.

Examples of the polyester amides and polyamides are the predominantly linear condensates obtained from polybasic, saturated and unsaturated carboxylic acids and the anhydrides thereof and polyfunctional saturated and unsaturated amino alcohols, diamines, polyamines and mixtures thereof.

Polyhydroxyl compounds already containing urethane or urea groups and optionally modified natural polyols, such as castor oil, carbohydrates, starch, may also be used. Addition products of alkylene oxides with phenol-formaldehyde resins or even with urea-formaldehyde resins may also be used in accordance with the present invention.

Representatives of these compounds used in accordance with the present invention are described, for example, in High Polymers, Vol.XVI, "Polyurethanes, Chemistry and Technology", by Saunders-Frisch, Interscience Publishers, New York, London, Vol. I, 1962, pages 32 to 42 and pages 44 to 54, and Vol. II, 1964, pages 5–6 and 198–199, and in Kunststoff-Handbuch, Vol. VII. Vieweg-Hochtlen, Carl Hanser-Verlag, Munich, 1966, for example on pages 45 to 71.

Other starting components which may optionally be used in accordance with the present invention are compounds containing at least two isocyanate-reactive hydrogen atoms and having a molecular weight of from 32 to 400. In this case, too, the compounds in question are compounds containing hydroxyl groups and/or amino groups and/or thiol groups and/or carboxyl groups, preferably compounds containing hydroxyl groups and/or amino groups which are used as chain-extenders or cross-linkers. These compounds generally contain from 2 to 8 isocyanate-reactive hydrogen atoms, preferably 2 or 3 such reactive hydrogen atoms.

Examples of such compounds include: ethylene glycol, 1,2- and 1,3-propylene glycol, 1,4- and 2,3-butylene glycol, 1,5-pentane diol, 1,6-hexane diol, 1,8-octane diol, neopentyl glycol, 1,4-bis-hydroxymethyl cyclohexane, 2-methyl-1,3-propane diol, glycerol, trimethylol propane, 1,2,6-hexane triol, trimethylol ethane, pentaerythritol, quinitol, mannitol, sorbitol, diethylene glycol, triethylene glycol, tetraethylene glycol, polyethylene glycols having a molecular weight of up to 400, dipropylene glycol, polypropylene glycols having a molecular weight of up to 400, dibutylene glycol, polybutylene glycols having a molecular weight of up to 400, 4,4'-dihydroxy diphenyl propane, dihydroxy methyl hydroquinone, ethanolamine, diethanolamine, triethanolamine, 3-aminopropanol, ethylene diamine, 1,3-diaminopropane, 1-mercapto-3-aminopropane, 4-hydroxy- or -aminophthalic acid, succinic acid, adipic acid, hydrazine, N,N'-dimethyl hydrazine, 4,4'-diaminodiphenyl methane, tolylene diamine, methylene-bis-chloroaniline, methylene-bis-anthranilic acid ester, diaminobenzoic acid esters and the isomeric chlorophenylene diamines.

In this case, too, it is possible to use mixtures of different compounds containing at least two isocyanate-reactive hydrogen atoms and having a molecular weight of from 32 to 400.

It is, of course, also possible to use the starter mixtures used in accordance with the present invention as chain-extenders or cross-linkers.

However, it is also possible in accordance with the present invention to use polyhydroxyl compounds containing high molecular weight polyadducts or polycondensates in finely dispersed or dissolved form. Such modified polyhydroxyl compounds are obtained by carrying out polyaddition reactions (for example reactions between polyisocyanates and amino-functional compounds) or polycondensation reactions (for example between formaldehyde and phenols and/or amines) directly in situ in the above-mentioned compounds containing hydroxyl groups. Such processes are described, for example, in German Auslegeschriften Nos. 1,168,075 and 1,260,142 and in German Offenlegungsschriften Nos. 2,324,134; 2,423,984; 2,512,385; 2,513,815; 2,550,796; 2,550,797; 2,550,833, and 2,550,862. However, it is also possible, in accordance with U.S. Pat. No. 3,869,413 or German Offenlegungsschrift No. 2,550,860, to mix an aqueous polymer dispersion with a polyhydroxyl compound and subsequently to remove the water from the mixture.

In cases where modified polyhydroxyl compounds of the type mentioned above are used as starting components in the polyisocyanate polyaddition process, polyurethane plastics having considerably improved mechanical properties are formed in many cases.

Water and/or readily volatile organic substances may be used as blowing agents in the production of foamed polyurethane plastics. Suitable organic blowing agents include acetone, ethyl acetate, halogen-substituted alkanes, such as methylene chloride, chloroform, ethylidene chloride, vinylidene chloride, monofluorotrichloromethane, chlorodifluoromethane and dichlorodifluoromethane, also butane, hexane, heptane or diethyl ether. A blowing effect may also be obtained by adding compounds which decompose at temperatures above room temperature giving off gases, for example nitrogen, for example azo-compounds, such as azoisobutyronitrile. Other examples of blowing agents and information on the use of blowing agents may be found in Kunststoff-Handbuch, Vol. VII, by Vieweg und Hochtlen, Carl-Hanser-Verlag, Munich 1966, for example on pages 108 and 109, 453 to 455 and 507 to 510.

According to the present invention, catalysts are also frequently used. Suitable known catalysts include tertiary amines, such as triethyl amine, tributyl amine, N-methyl morpholine, N-ethyl morpholine, N-cocomorpholine, N,N,N',N'-tetramethyl ethylene diamine, 1,4-diazabicyclo-(2,2,2)-octane, N-methyl-N'-dimethyl aminoethyl piperazine, N,N,-dimethyl benzyl amine, bis-(N,N-diethyl amino ethyl)-adipate, N,N-diethyl benzyl amine, pentamethyl diethylene triamine, N,N-dimethyl cyclohexyl amine, N,N,N',N'-tetramethyl-1,3-butane diamine, N,N-dimethyl-β-phenyl ethyl amine, 1,2-dimethyl imidazole and 2-methyl imidazole and the like. Other suitable catalysts are known Mannich bases of secondary amines, such as dimethyl amine, and aldehydes, preferably formaldehyde, or ketones, such as acetone, methyl ethyl ketone or cyclohexanone, and phenols, such as phenol, nonyl phenol or bisphenol.

Examples of tertiary amines containing isocyanate-reactive hydrogen atoms which may be used as catalysts include: triethanolamine, triisopropanol amine, N-methyl diethanolamine, N-ethyl diethanolamine and N,N-dimethyl ethanolamine, as well as the reaction products thereof with alkylene oxides, such as propylene oxide and/or ethylene oxide.

Other suitable catalysts are silaamines having carbon-silicon bonds of the type described, for example, in German Pat. No. 1,229,290 (corresponding to U.S. Pat. No. 3,620,984). These include 2,2,4-trimethyl-2-silamorpholine and 1,3-diethyl aminomethyl tetramethyl disiloxane.

Other suitable catalysts are nitrogen-containing bases, such as tetraalkyl ammonium hydroxides; alkali metal hydroxides, such as sodium hydroxide; alkali metal phenolates, such as sodium phenolate; or alkali metal alcoholates, such as sodium methylate. Hexahydrotriazines may also be used as catalysts.

According to the present invention, organometallic compounds, especially organotin compounds, may also be used as catalysts.

Preferred organotin compounds are tin (II) salts of carboxylic acids, such as tin (II) acetate, tin (II) octoate, tin (II) ethyl hexoate and tin (II) laurate, and the tin (IV) compounds, for example dibutyl tin oxide, dibutyl tin dichloride, dibutyl tin diacetate, dibutyl tin dilaurate, dibutyl tin maleate or dioctyl tin diacetate. It is, of course, possible to use the above-mentioned catalysts in the form of mixtures.

Further representatives of catalysts suitable for use in accordance with the present invention and details on the way in which the catalysts work may be found in Kunststoff-Handbuch, Vol. VII, by Vieweg und Hochtlen, Carl-Hanser-Verlag, Munich, 1966, for example on pages 96 to 102.

The catalysts are generally used in quantities of from about 0.001 to 10%, by weight, based on the quantity of compounds having at least two isocyanate-reactive hydrogen atoms and a molecular weight from 400 to 10,000.

According to the present invention, surface-active additives, such as emulsifiers and foam stabilizers, may also be used. Examples of emulsifiers are the sodium salts of castor oil sulphonates or salts of fatty acids with amines, such as diethyl amine/oleic acid or diethanolamine/stearic acid. Alkali metal or ammonium salts of sulphonic acids, such as those of dodecyl benzene sulphonic acid or dinaphthyl methane disulphonic acid, or of fatty acids, such as ricinoleic acid, or of polymeric fatty acids, may also be used as surface-active additives.

Suitable foam stabilizers are above all polyether siloxanes, especially water-soluble types. These compounds generally have a structure in which a copolymer of ethylene oxide and propylene oxide is attached to a polydimethyl siloxane radical. Foam stabilizers of this type are described, for example, in U.S. Pat. Nos. 2,834,748; 2,917,480 and 3,629,308.

According to the present invention, it is also possible to use reaction retarders, for example substances which are acid in reaction, such as hydrochloric acid or organic acid halides; known cell regulators, such as paraffins, fatty alcohols or dimethyl polysiloxanes; pigments of dyes, known flameproofing agents, such as trischlorethyl phosphate, tricresyl phosphate or ammonium phosphate and polyphosphate; stabilizers against the effects of ageing and weathering; plasticizers; substances having fungistatic and bacteriostatic effects; and fillers, such as barium sulphate, kieselguhr, carbon black or prepared chalk.

Other examples of the surface-active additives and foam stabilizers optionally used in accordance with the present invention and of cell regulators, reaction retarders, stabilizers, flameproofing substances, plasticizers, dyes, fillers, substances having fungistatic and bacteriostatic effects, and also details on the way in which these additives are to be used and how they work, may be found in Kunstsoff-Handbuch, Vol. VII, published by Vieweg und Hochtlen, Carl-Hanser-Verlag, Munich, 1966, for example on pages 103 to 113.

According to the present invention, the reaction components may be reacted by the known single-stage process, by the prepolymer process or by the semi-prepolymer process, in many cases using machines of the type described, for example, in U.S. Pat. No. 2,764,565. Particulars of processing equipment suitable for use in accordance with the present invention may be found, for example, on pages 121 and 205 of Kunststoff-Handbuch, Vol. VII, published by Vieweg und Hochtlen, Carl-Hanzer-Verlag, Munich, 1966.

In the production of foams, the foaming reaction is preferably carried out in molds in accordance with the present invention. To this end, the reaction mixture is introduced into a mold. Suitable mold materials are metals, for example aluminum, or plastics, for example epoxide resins. Inside the mold, the foamable reaction mixture foams and forms the molding. In-mold foaming may be carried out in such a way that the molding has a cellular structure at its surface, or even in such a way that the molding has a compact skin and a cellular core. According to the present invention, it is possible in this connection to introduce such a quantity of foamable reaction mixture into the mold that the foam formed just fills the mold. However, it is also possible to introduce into the mold more foamable reaction mixture than is required for filling the mold with foam. This technique is known as "overcharging" and is known, for example, from U.S. Pat. Nos. 3,178,490 and 3,182,104.

Known "external release agents", such as silicone oils, are frequently used for in-mold foaming. However, it is also possible to use so-called "internal release agents", optionally in admixture with external release agents, such as are known, for example, from German Offenlegungsschriften Nos. 2,121,670 and 2,307,589.

According to the present invention, cold-hardening foams may also be produced (cf. British Pat. No. 1,162,517, German Offenlegungsschrift No. 2,153,086).

However, it is, of course, also possible to produce foams by block foaming or by the known laminator process.

To sum up, it may be stated that the polyethers produced in accordance with the present invention show the following significant advantages over conventional polyethers:

For the same functionality and for a comparable hydroxyl number, the polyethers according to the present invention show a reduced viscosity compared to conventional polyethers, such as the trimethylol propane polyethers or the polyethers based on saccharose or saccharose/polyol mixtures. This property enables the polyethers to be reacted under favorable conditions to form polyurethane foams. The low viscosity provides for an increased pumping capacity to the mixing heads of conventional foaming machines and also for more complete, faster admixture with the isocyanate component. Accordingly, the reaction mixture may be applied in a relatively short time or, in other words, more reaction mixture may be applied and distributed more uniformly in the same time.

In addition, the low viscosity of the polyethers according to the present invention provides for improved fluidity of the reaction mixtures during the foaming process. In this way, the gross density of the resulting polyurethane foams is distributed more uniformly which in turn provides for higher compressive strength.

It is possible to use a more highly functional polyether for the same viscosity of the reaction mixture. This results in quicker hardening of the foam.

The commercial production of the polyethers is also simplified. The starter mixtures used in accordance with the present invention are viscous to low viscosity liquids, even without the addition of water or low viscosity polyols. For example, the viscosity of a mixture having an average functionality of 4.6 amounts to 1195 cP at 80° C. and to 324 cP at 100° C. Secondary reactions which occur as a result of the inadequate stirrability of the reaction mixtures, such as caramelization, carbonization or the formation of inner ethers, are avoided. One economic advantage of formose polyethers over formitol polyethers is that the hydrogenation costs for reducing the formose into formitol are eliminated.

The tests on which the following Examples are based were carried out in an autoclave which was provided with a heating and cooling system, a stirrer, a means for displacing the air present (for example, vacuum connection and nitrogen inlet pipe), an apparatus for azeotropic dehydration and a metering unit for the alkylene oxide.

The process according to the present invention is illustrated by the following Examples. Unless otherwise indicated, the figures quoted represent parts, by weight, and percent, by weight.

EXAMPLE 1

(A) Production of the formose

The formose was produced in strict accordance with Example 1 of German Offenlegungsschrift No. 2,639,084 in the form of a ten-fold semi-commercial batch, but with the difference that formation of the formose was stopped at a residual formaldehyde content of 1.7% as opposed to 1.3% and also that the lead and potassium ions were fixed to an acid standard commercialgrade cation exchanger instead of precipitating the lead(II)ions with potassium carbonate. As a result of this measure, the formose solution was completely freed from lead and potassium ions and was therefore partially desalted.

A formose syrup containing 4% water is obtained which has a viscosity of 114,000 mPas at 35° C. and the following molecular distribution:

Compounds containing 2 carbon atoms: 3.3%
Compounds containing 3 carbon atoms: 7.4%
Compounds containing 4 carbon atoms: 16.5%
Compounds containing 5 carbon atoms: 36.0%
Compounds containing 6 carbon atoms: 27.0%
Compounds containing 7 carbon atoms: 8.6%
Compounds containing 8 carbon atoms: 1.2%

This formose has an average molecular weight of 158 and an average hydroxyl functionality of 4.14. The content of reducing compounds, expressed as glucose, amounts to 71%.

(B) Process according to the present invention

Four batches (a) through (d) of 100 g of the formose syrup are mixed while stirring under nitrogen at room temperature with separate quantities of 0.5 g of a complex of 1 mol of boron trifluoride and 1 mol of acetic acid. The four mixtures are thoroughly stirred under nitrogen and the following quantities of propylene oxide are slowly and uniformly added dropwise over a period of 2 hours at 49° C:

(a) 58 g of propylene oxide (1 mol)
(b) 87 g of propylene oxide (1.5 mols)
(c) 116 g of propylene oxide (2 mols)
(d) 232 g of propylene oxide (4 mols).

After adjusting the pH value to 7.3 sodium hydroxide or aqueous 25% ammonia solution, mixtures (a) to (d) are vacuum distilled at 50° C. from traces of propylene oxide and small quantities of water. Formose polyethers having a surprisingly low viscosity and a small number of reducing groups are obtained.

(a) Yield: 155g; OH-number: 880; acid number: 0.7; viscosity: 19000 mPas/35° C; reducing fraction (expressed as glucose polyether): 19.8%. The low content of reducing sugar fractions shows that the carbonyl groups in the formose were surprisingly acetalized or ketalized to a considerable extent during propoxylation, presumably by the ring-opening addition of propylene oxide to 1,3-dioxolane derivatives as the primary step.

(b) Yield: 183g; OH-number: 730; acid number: 0.6; viscosity: 16840 mPas/35° C; proportion of reducing compounds: 14.6%.

(c) Yield: 207 g; OH-number: 640; acid number: 0.6; viscosity: 5600 mPas/35° C; proportion of reducing compounds: 12.2%.

(d) Yield: 315 g; OH-number: 420; acid number: 0.6; viscosity: 3890 mPas/35° C; proportion of reducing compounds: 3.5%.

Simple calculation shows that, in mixture (a), approximately 56%, in mixture (b) approximately 63%, in mixture (c) approximately 64% and, in mixture (d), approximately 80% of the aldehyde or keto groups present in the formose are acetalized or ketalized in the process according to the present invention. In view of the high concentration of free OH-groups and the 4% by weight of water in the starter mixture, which groups compete with the carbonyl groups for the reaction with propylene oxide, this is an extremely surprising result.

Although an only partly desalted formose, i.e. a formose from which only the metal cations were removed, was used in the present Example, whereas the anions formed by Cannizzaro reaction and crossed Cannizzaro reaction (formic acid, lactic acid and various sugar acids) were left in the reaction mixture, the low acid numbers of the products obtained indicate that most of the acids present were converted into polyether esters containing terminal hydroxyl groups.

All the polyether mixtures (a) to (d) are more compatible than dehydrated crude formoses with high molecular weight and low molecular weight polyhydroxyl compounds as well as with isocyanates. Another factor of particular importance is that the polyethers obtained in accordance with (a) to (d) are much more active when reacted with polyisocyanates than formose polyethers produced in the conventional way by $OH^\ominus$—catalysis in the presence of sodium hydroxide or potassium hydroxide. The Lewis acid-catalyzed polyaddition of the propylene oxide with formose would appear to take place fairly selectively in accordance with the following scheme:

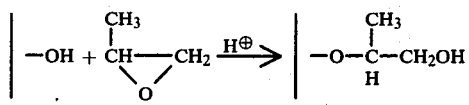

The present reaction leads to primary hydroxyl groups, while the base-catalyzed polyaddition reaction takes place statistically so that at least 50% of secondary hydroxyl groups are present in the polyether. In addition, the $OH^\ominus$—catalyzed reaction leads to dark-colored products and is accompanied by decomposition reactions of the formoses.

Rigid to semi-rigid polyurethane foams may be produced from the polyether mixtures (a) to (d) in accordance with known formulations.

In the polyaddition of approximately 2500 g of propylene oxide in accordance with (d) with 100 g of formose in the presence of increased quantities of $BF_3$-acetate (approximately 5.5 g), polyethers having OH-numbers of from 56 to 60 are obtained and are eminently suitable for the production of flexible foams.

EXAMPLE 2

The procedure is as in Example 1, except that a formose produced in accordance with Example 1(A) is used where the condensation of the formaldehyde has been stopped at a residual formaldehyde content of 1.3%. The formose freed from cations still contains approximately 1.5% by weight, of formic acid, lactic acid and sugar acid and shows the following molecular distribution:

Compounds containing 2 carbon atoms: 0.3%
Compounds containing 3 carbon atoms: 2.1%
Compounds containing 4 carbon atoms: 4.4%
Compounds containing 5 carbon atoms: 25.2%
Compounds containing 6 carbon atoms: 45.1%
Compounds containing 7 and more carbon atoms: 22.9%

The formose has an average molecular weight of 167.5, an average hydroxyl functionality of 4.79 and an OH-number of 1524. The proportion of reducing sugars (expressed as glucose) amounts to 70%.

(a) Reaction of the formose syrup containing approximately 3.8% of water in accordance with Example 1(B), variant (d), gives a formose polyether containing a reducing fraction (expressed as glucose polyether) of only 8.2%, having an OH-number of 425, and an acid number of 0.8. The polyether has a viscosity of 5500 mPas/35° C.

(b) A total of 2350 g of propylene oxide is added dropwise with stirring under nitrogen to a mixture of 100 g of the above formose syrup (water content 3.8%) and 2 g of the complex of 1 mol of boron trifluoride and 1 mol of acetic acid. After the addition of 235 g of propylene oxide in each case, further quantities of 0.5 g of the catalyst are introduced into the reaction mixture. The polyether obtained has an OH-number of 60 and a reducing fraction of only 0.4%.

Variant (a) of this Example is repeated using the following catalysts instead of 0.5 g of boron trifluoride acetate:

(a) (1) 0.8 g of an adduct of 1 mol of boron trifluoride and 1 mol of acetic acid anhydride;

(a) (2) 0.9 g of an adduct of 1 mol of boron trifluoride and 1 mol of the mixed anhydride of acetic acid and caproic acid;

(a) (3) 1.2 g of an adduct of 1 mol of boron trifluoride and 1 mol of the mixed anhydride of benzoic acid and acetic acid;

(a) (4) 1.8 g of the addition product of 1 mol of boron trifluoride and 1 mol of the mixed anhydride of acetic acid and oleic acid;

(a) (5) 0.85 g of the addition product of 1 mol of boron trifluoride and 1 mol of maleic acid anhydride dissolved in 3 g of acetic acid;

(a) (6) 3.4 g of an adduct of 1 mol of boron trifluoride and 1 mol of hexahydrophthalic acid anhydride;

(a) (7) 2.5 g of an adduct of 1 mol of trimellitic acid anhydride and 2 mols of boron trifluoride dissolved in 4 g of acetic acid.

In every case, polyaddition of the propylene oxide with the starter mixture takes place at substantially the same velocity as in variant (a); the yield amounts to from about 95 to 98% (the loss of yield, amounting to from approximately 2 to 5% of propylene oxide, is attributable to the fact that a small proportion of the propylene oxide is entrained by the inert gas stream).

After working up of the products obtained in accordance with (a) and (b) and (a) (1) to (a) (7), fresh catalysts may be added, after which polyethylene glycol segments may be attached to the propylene glycol segments of the polyether by the addition of ethylene oxide in an autoclave at 55° C./ 0.4 bar excess pressure. It is also possible to add other cyclic ethers, for example epichlorohydrin, styrene oxide, cyclohexene oxide or vinyl oxirane, to the polypropylene oxide in this second stage.

EXAMPLE 3

Production of the formose

The formose is produced in accordance with Example 2 of German Offenlegungsschrift No. 2,639,084. As described in that Example, formation of the formose is stopped at a residual formaldehyde content of 8%. The formose is then freed from cations and concentrated in accordance with Example 1(A).

A formose syrup containing approximately 3% of water is obtained which has a viscosity of 12500 mPas at 35° C., an average molecular weight of 104, an average hydroxyl functionality of 2.39, an OH-number of 1260 and a sugar content of 75%, expressed as glucose. The formose has the following molecular composition:
Compounds containing 2 carbon atoms: 16.8%
Compounds containing 3 carbon atoms: 21.0%
Compounds containing 4 carbon atoms: 29.9%
Compounds containing 5 carbon atoms: 25.1%
Compounds containing 6 carbon atoms: 7.2%

100 g of the formose syrup are reacted with 116 g of propylene oxide in accordance with the procedure of Example 1(B). A formose polyether having a sugar content of only 13.4% (expressed as glucose polyether) is obtained. The polyether has a viscosity of 2400 mPas at 35° C., an Oh-number of 380 and an acid number of 0.7.

Examples 4 to 6 below show that, where the starter mixture has a relatively high water content, it is only the particularly preferred complexes of boron trifluoride and carboxylic acids or carboxylic acid anhydride according to the present invention which gives satisfactory results. Other acid catalysts only give low propoxylation yields. Due to the relatively large quantities of water still present in the reaction mixture, the proportion of acetalated or ketalated carbonyl groups in the formose polyethers is very small in all Examples 4 to 6 (from approximately 8 to 14% of the reduction equivalents present in the formose).

EXAMPLE 4

100 g of a formose produced in accordance with German Offenlegungsschrift No. 2,721,186 (Example 1), which contains 11.4% of water and has a sugar content of 63.5%, expressed as glucose, are mixed with 0.5 ml of perfluorobutane sulphonic acid. The resulting mixture is heated to 60° C. 58 g (1 mol) of propylene oxide are added dropwise over a period of 10 hours at that temperature under a gentle stream of nitrogen. The reaction mixture is neutralized with dilute NaOH and subsequently concentrated in vacuo (25 Torr) at 50° C. 114 g of a propoxylated formose are obtained, containing 8.7% of water and 58.6% of sugar, expressed as glucose (conversion, based on propylene oxide: 24.1%).

EXAMPLE 5

100 g of formose of Example 4 are heated to 40° C. with 1 ml of boron trifluoride etherate and 0.3 g of 40% hydrochloric acid. 58 g of propylene oxide are then added dropwise over a period of 13 hours at from 40° to 60° C. under a gentle stream of nitrogen. The reaction mixture is then concentrated in vacuo (25 Torr) at 50° C. 108.5 g of a propoxylated formose is obtained, containing 7.5% of water and 53.1% of sugar, expressed as glucose. Conversion (based on propylene oxide): approximately 13.8%.

EXAMPLE 6

200 parts of a 50% aqueous solution of the formose used in Example 2 are mixed with 287 parts of a 30% formalin solution. The resulting mixture is concentrated in a water jet vacuum to a water content of 3.5%. 1.2 parts of boron trifluoride acetate are added to the semiacetalated formose thus obtained in the complete absence of air, followed by alkoxylation with 196 parts of propylene oxide in the same way as in Example 1. 370 parts of a formose polyether containing acetal segments and polyacetal segments and having an OH-number of approximately 405 and an acid number of 1.4 are obtained. It is particularly surprising that the product contains only about 4% of the cyclic 1,3-dioxolane:

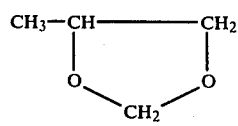

as secondary products.

EXAMPLE 7

This Example demonstrates the use of α-aldolated formoses (i.e. branched sugars) as a starter mixture for the process according to the present invention.

100 g of an α-aldolated formose produced in accordance with Example 25(a) of German Offenlegungsschrift No. 2,721,186 are alkoxylated with 232 g of propylene oxide in accordance with Example 1(B). 312 g of a yellowish polyether having an OH-number of 445 are obtained.

EXAMPLE 8

This Example demonstrates the use of mixtures of formose and natural mono- or di-saccharides and invert sugars as starter mixture for the process according to the present invention.

Quantities of 100 g of a 50% aqueous solution of the formose used in Example 2 are mixed with quantities of 50 g of the following saccharides and the clear solutions obtained are concentrated in a water jet vacuum to a water content of 3.5%:
 (a) 50 g of cane sugar
 (b) 50 g of D-glucose
 (c) 50 g of lactose
 (d) 50 g of bee's honey
 (e) 50 g of a sugar mixture produced by the enzymatic degradation of corn starch
 (f) 50 g of a synthetic invert sugar produced by splitting cane sugar on an acid ion exchanger.

Mixtures (a) to (f) are alkoxylated under nitrogen in the absence of air with 232 g of propylene oxide in the presence of 0.8 g of the addition product of 1 mol of boron trifluoride and 1 mol of acetic acid anhydride in the same way as described in Example 1(B). Polyether polyols having the following hydroxyl numbers are obtained in the following yields:
 (a) 318 g; OH-number: 460
 (b) 319 g; OH-number: 463
 (c) 315 g; OH-number: 480
 (d) 309 g; OH-number: 489
 (e) 305 g; OH-number: 485
 (f) 310 g; OH-number: 479.

The yellowish to honey-colored polyether polyols thus obtained have acid numbers of from 0.6 to 0.9.

EXAMPLE 9

Production of the formose

The formose was produced as follows using calcium hydroxide as catalyst and the formose described in Example 1(A) as co-catalyst:

81 g of an approximately 90% formose syrup produced in accordance with Example 1(A) as co-catalyst are dissolved in 2860 g of a 37% aqueous formaldehyde solution. The solution is then heated to 90° C. and 70 g of calcium hdyroxide are uniformly introduced in small portions over a period of 4.5 hours (pH from 8.8 to 8.3). The cooled solution is freed first from calcium ions on a conventional commercial-grade acid ion exchanger and then from formic acid, lactic acid and sugar acid on a basic ion exchanger and concentrated to a water content of 3.5% in a rotary evaporator at 58° C./16 Torr. Yield: 1005 g of a yellow formose containing approximately 3.5% of water.

Due to the use of calcium hydroxide as catalyst for condensation of the formaldehyde, a large proportion of the carbonyl groups is reduced into hydroxyl groups by crossed Cannizzaro reaction, so that the reaction mixture has a sugar content of only 37.2%, expressed as glucose. The formose thus obtained has an average molecular weight of 146, an average hydroxyl functionality of 4.06 and an OH-number of 1490. It has the following molecular distribution:
Compounds containing 2 carbon atoms: 1.17%
Compounds containing 3 carbon atoms: 2.21%
Compounds containing 4 carbon atoms: 10.09%
Compounds containing 5 carbon atoms: 8.05%
Compounds containing 6 carbon atoms: 28.27%
Compounds containing 7 and more carbon atoms: 50.21%

100 g of the fully desalted formose containing 3.5% water are alkoxylated with 232 g of propylene oxide at from 58° to 60° C. in the presence of 0.8 g of boron trifluoride acetate in the same way as in Example 1(B). 327 g of a polyether having an OH-number of 465 and an acid number of 0.7 are obtained.

The polyether polyols produced in accordance with Examples 1 to 9 are eminently suitable for the production of polyurethane foams, particularly rigid foams. By virtue of the low content of free aldehyde and keto groups thereof, the process products according to the present invention have the advantage of not entering into any caramelization reactions during the foaming reaction which would result in the evolution of an unpleasant odor. The polyurethane foams produced from them also show no core discoloration.

EXAMPLE 10

89 g of a polyol formulation produced from 95 parts of the formose polyether having an OH-number of 425 according to Example 7(a), 5 parts of an ethylamine-started polyethylene oxide having an OH-number of 490, 2.1 parts of water, 1.5 parts of a standard commercial-grade foam stabilizer based on a siloxane-oxyalkylene copolymer and 2.1 parts of dimethyl cyclohexylamine, are thoroughly mixed with 38 g of dichlorodifluoromethane and 129 g of a technical diphenyl methane diisocyanate having an isocyanate content of 31% by means of a high-speed stirrer.

A rigid, yellow, closed-cell polyurethane foam having a density of 27 kg/m$^3$ is obtained.

EXAMPLE 11

54 g of tolylene diisocyanate (80% of 2,4- and 20% of 2,6-isomer) are stirred by means of a high-speed stirrer into a mixture of 100 g of the formose polyether having an OH-number of 60 according to Example 7(b), 4 g of water, 1.5 parts of a standard commercial-grade foam stabilizer based on a siloxane-oxyalkylene copolymer, 0.25 part of triethylene diamine and 0.4 part of the tin-(II)salt of 2-ethylcaproic acid. After a cream time of about 10 seconds, the foaming reaction begins and results in the formation of a white, flexible, open-cell elastic polyurethane foam having good physical properties and a density of approximately 26 kg/m$^3$.

What is claimed is:

1. A process for the production of polyether polyols having an average molecular weight of from 200 to 10,000 and an average hydroxyl functionality of from 2.0 to 7.0, comprising reacting one or more cyclic ethers, optionally successively, with a starter comprising:

(A) formose which is optionally α-aldolized; or
(B) liquid mixtures of:

(a) high molecular weight and/or low molecular weight polyhydroxyl compounds and/or mono- or di-saccharides and/or natural or synthetic invert sugars; and (b) formose which is optionally α-aldolized in the presence of an acid catalyst.

2. The process of claim 1 wherein from 20 to 80% by weight of solutions of crystalline mono- or di-saccharides and/or natural or synthetic invert sugars in formose are used as starter.

3. The process of claim 2 wherein from 30 to 70% by weight solutions of crystalline mono- or di-saccharides and/or natural or artificial invert sugars in formose are used as starter.

4. The process of claim 1 wherein the starter contains from 2 to 100% by weight based on the total starter mixture, of dihydric or polyhydric alcohols having a molecular weight of from 62 to 300 and/or polyether, polyester, polyacetal and/or polycarbonate polyols having a molecular weight of from 300 to 4000.

5. The process of claim 1 wherein formoses having a molecular weight of from 92 to 360 are used.

6. The process of claim 1 wherein formoses having a content of reducing compounds, expressed as glucose, of from 4 to 85% by weight are used.

7. The process of claim 1 wherein ethylene oxide and/or propylene oxide are used as cyclic ethers.

8. The process of claim 1 wherein an adduct of a carboxylic acid or carboxylic acid anhydride with boron trifluoride is used as the acid catalyst.

9. The process of claim 8, wherein the starter contains from 0.5 to 20% by weight of water.

10. The process of claim 1 wherein the starter contains from 0.5 to 4% by weight of water.

11. In a process for the production of optionally cellular polyurethane plastics by reacting:

(a) polyisocyanates; with (b) relatively high molecular weight compounds containing isocyanate-reactive hydrogen atoms; and optionally, (c) chain-extenders; optionally in the presence of (d) blowing agents, catalysts and other known additives;

the improvement which comprises using the polyether polyols as component (b) which are produced by a process comprising reacting one or more cyclic ethers, optionally successively, with a starter comprising:

(A) formose which is optionally α-aldolized; or (B) liquid mixtures of:

(a) high molecular weight and/or low molecular weight polyhydroxyl compounds and/or mono- or di-saccharides and/or natural or synthetic invert sugars; and (b) formose which is optionally α-aldolized in the presence of an acid catalyst.

* * * * *